(12) United States Patent
Doll et al.

(10) Patent No.: US 8,945,097 B2
(45) Date of Patent: Feb. 3, 2015

(54) MEDICAL INSTRUMENT

(75) Inventors: Frank Doll, Talheim (DE); Martin Hahn, Altheim (DE)

(73) Assignee: Karl Storz GmbH & Co. KG (DE)

(*) Notice: Subject to any disclaimer, the term of this patent is extended or adjusted under 35 U.S.C. 154(b) by 784 days.

(21) Appl. No.: 13/045,235

(22) Filed: Mar. 10, 2011

(65) Prior Publication Data

US 2011/0264079 A1 Oct. 27, 2011

(30) Foreign Application Priority Data

Mar. 10, 2010 (DE) .......................... 10 2010 010 947

(51) Int. Cl.
- A61B 17/00 (2006.01)
- A61B 17/42 (2006.01)
- A61B 17/29 (2006.01)

(52) U.S. Cl.
CPC ... A61B 17/4241 (2013.01); A61B 2017/00853 (2013.01); A61B 2017/2927 (2013.01); A61B 2017/2934 (2013.01)
USPC .......................................................... 606/1

(58) Field of Classification Search
USPC .......................................................... 606/1
See application file for complete search history.

(56) References Cited

U.S. PATENT DOCUMENTS

| | | | |
|---|---|---|---|
| 5,237,985 A | 8/1993 | Hodgson et al. | |
| 5,382,252 A | 1/1995 | Failla et al. | |
| 7,473,254 B2 | 1/2009 | White et al. | |
| 7,699,835 B2 * | 4/2010 | Lee et al. | 606/1 |
| 8,105,320 B2 * | 1/2012 | Manzo | 606/1 |
| 2004/0127890 A1* | 7/2004 | Bacher | 606/1 |
| 2008/0147113 A1* | 6/2008 | Nobis et al. | 606/205 |

FOREIGN PATENT DOCUMENTS

| | | |
|---|---|---|
| DE | 202004019868 U1 | 2/2005 |
| EP | 0606531 A2 | 7/1994 |
| EP | 1695669 A1 | 8/2006 |

OTHER PUBLICATIONS

European Search Report; Application No. EP 11 15 7250; Issued: Jul. 18, 2011; 4 pages.
German Search Report; Application No. 10 2010 010 947.9; Nov. 16, 2010; 4 pages.

* cited by examiner

*Primary Examiner* — William Thomson
*Assistant Examiner* — John R Downey
(74) *Attorney, Agent, or Firm* — St. Onge Steward Johnston & Reens LLC

(57) ABSTRACT

A medical instrument with a proximal instrument part and a distal instrument part that are connected with one another by an elongated shaft. The distal instrument part includes a pivot element that is mounted to pivot with respect to the shaft and that can pivot by a translationally moveable actuation element. The pivot element is coupled with the actuating element by a coupling element, so that the coupling element is in a hinged connection with the pivot element by a first hinged connection and with the actuation element by a second hinged connection. The second hinged connection is controlled by at least one nonlinear guide formed by the distal instrument part in such a way that the pivot element can pivot both in the one pivot direction and in the other pivot direction. The actuating element is configured to be suitable for control by the nonlinear guide.

11 Claims, 6 Drawing Sheets

MEDICAL INSTRUMENT

CROSS-REFERENCE TO RELATED APPLICATIONS

The present application claims priority of German patent application No. 10 2010 010 947.9 filed on Mar. 10, 2010, the content of which is incorporated herein by reference.

FIELD OF THE INVENTION

The invention is in the field of medical technology and relates by its classification to a medical instrument with a proximal instrument part and a distal instrument part that are connected to one another by an elongated shaft.

BACKGROUND OF THE INVENTION

Generic medical instruments are available in the marketplace in great number and have already been amply described in the specialized patent literature. We refer merely by way of example, in this connection, to German utility model DE 202004019868 UI and to the Clermont-Ferrand Uterus Manipulator Model (apparatus no. 26168 D), marketed by the applicant, and its Tintara Uterus Manipulator (apparatus no. 26168 TN).

Conversely, it is the object of the present invention to further develop a generic medical instrument in advantageous manner.

SUMMARY OF THE INVENTION

This and other objects are fulfilled according to the proposal of the invention by means of a medical instrument with the properties of the independent claim. Advantageous embodiments of the invention are indicated by the properties of the associated claims.

According to the present invention, a medical instrument includes a proximal instrument part and a distal instrument part that are connected to one another by an elongated shaft, which is for example tubular in shape. The distal instrument part comprises a pivot element that is mounted so that it can pivot around a pivot axis with respect to the longitudinal direction or longitudinal axis of the shaft and that can rotate by means of a translationally movable actuation element, for example a push-pull rod.

The medical instrument is distinguished essentially in that the pivot element is coupled with the actuation element by means of at least one coupling element, so that the at least one coupling element has a hinged connection in each case, with the pivot element by means of a first hinged connection and with the actuation element by a second hinged connection. The first hinged connection of the coupling element connects the coupling element outside the pivot axis of the pivot element with said pivot element, so that torque can be transmitted onto the pivot element by the coupling element and the pivot element can be pivoted by the coupling element. The first hinged connection thus follows the pivot motion of the pivot part. The second hinged connection of the coupling element is controlled (directly or indirectly) by at least one nonlinear guide formed by the distal instrument part, in such a way that the pivot element can pivot both in the one pivot direction and in the other pivot direction. In addition, the actuation element is configured so that it is suited for guidance by the nonlinear guide, so that it can follow the movement track prescribed by the nonlinear guide. The actuation element, for this purpose, can comprise a distal end portion, for example, which is hinged onto the other portion of the actuation element so that it can pivot. Alternatively, it is also possible, for example, for the actuation element to be of flexible configuration.

The inventive medical instrument thus makes possible in advantageous manner a pivoting of the pivot element both in one pivot direction and in another pivot direction. This is accomplished in technically simplified manner by the at least one coupling element to transmit torque onto the pivot element, said coupling element being hinged both on the pivot element and on the actuation element, so that the hinged connection between the coupling element and the actuation element is controlled in appropriate manner directly or indirectly by a nonlinear guide.

In an advantageous embodiment of the medical instrument, the nonlinear guide is of angular configuration and includes a first portion that extends along the longitudinal axis defined by the shaft, hereinafter referred to as the "longitudinal portion," and a second portion extending diagonally to the longitudinal axis, hereinafter called the "diagonal portion." The diagonal portion here is placed in relation to the longitudinal axis in such a way that torque can be transmitted onto the pivot element by means of the first hinged connection between the coupling element and the pivot element.

As already described above, in the inventive medical instrument the second hinged connection of the coupling element can be controlled directly by the nonlinear guide. In this case it can be especially advantageous if the nonlinear guide is configured in the form of a connecting link guide, whereby the second hinged device of the coupling element can comprise for this purpose at least one hinged member that grips as a sliding pin in the connecting link guide. Thanks to this feature, a direct control of the second hinge connection can be realized in especially simple manner.

Alternatively, it is also possible for the second hinged connection of the coupling element to be controlled merely indirectly by the nonlinear guide. In particular, in this case the actuation element, for example, can be controlled by the nonlinear guide to obtain an indirect control of the second hinged connection by the nonlinear guide.

In another advantageous embodiment of the medical instrument the at least one coupling part has an arched configuration. Because of this feature, it becomes possible to pivot the pivot element over a relatively large pivot range, so that the arch-shaped coupling part can be controlled by a pivot shaft of the pivot element without running the risk of a collision between the coupling element and the pivot shaft.

In another advantageous embodiment of the medical instrument the pivot element, starting from a middle position, can pivot by at least 90 degrees in one pivot direction and at least 90 degrees in the other direction, and so because of this feature an especially large pivot range is realized for practical application.

The invention is now described in more detail on the basis of one embodiment, with reference to the appended drawings.

DETAILED DESCRIPTION OF THE INVENTION

Figure 1:
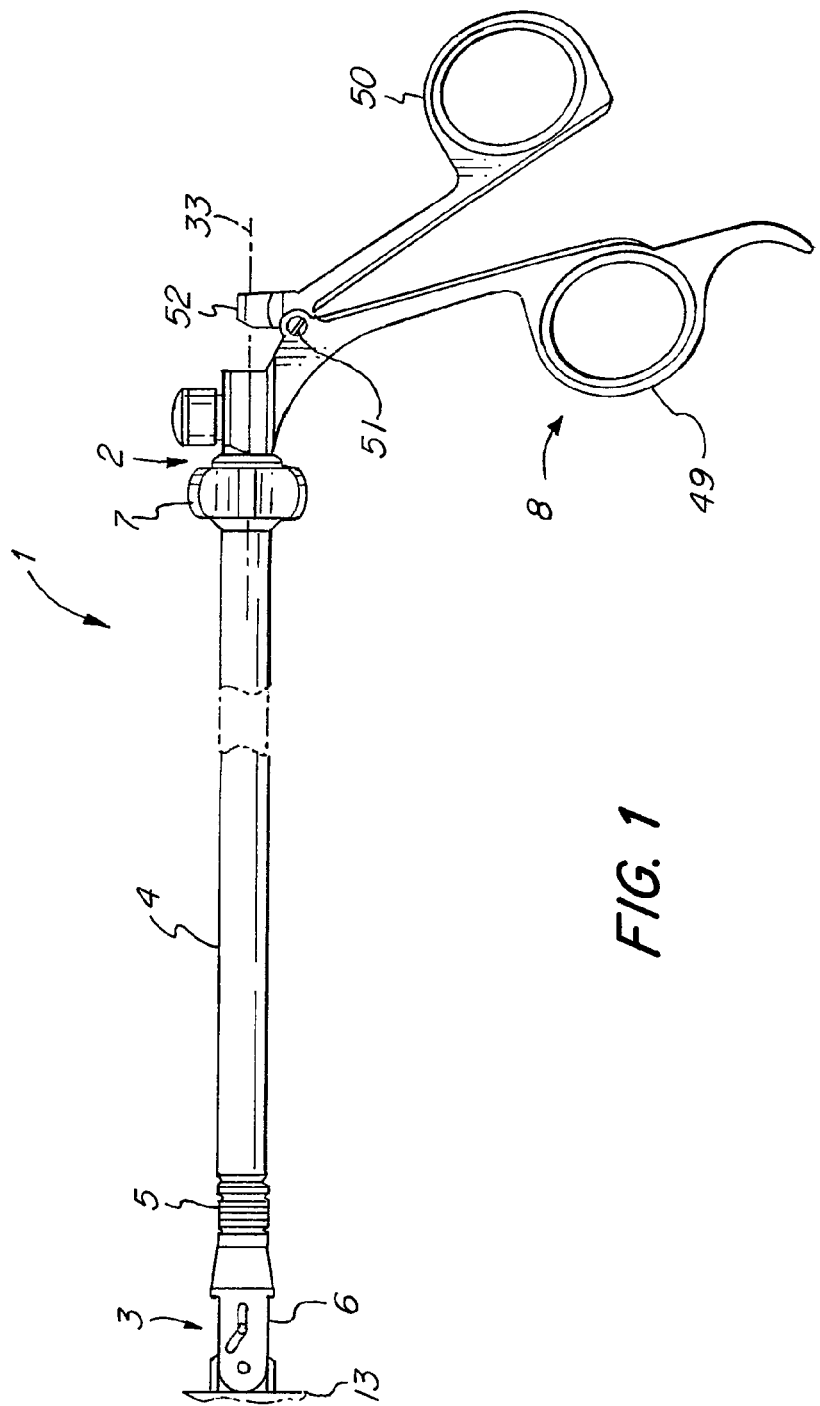
FIG. 1 shows an embodiment of the inventive instrument in a perspective side view.
Figure 2:
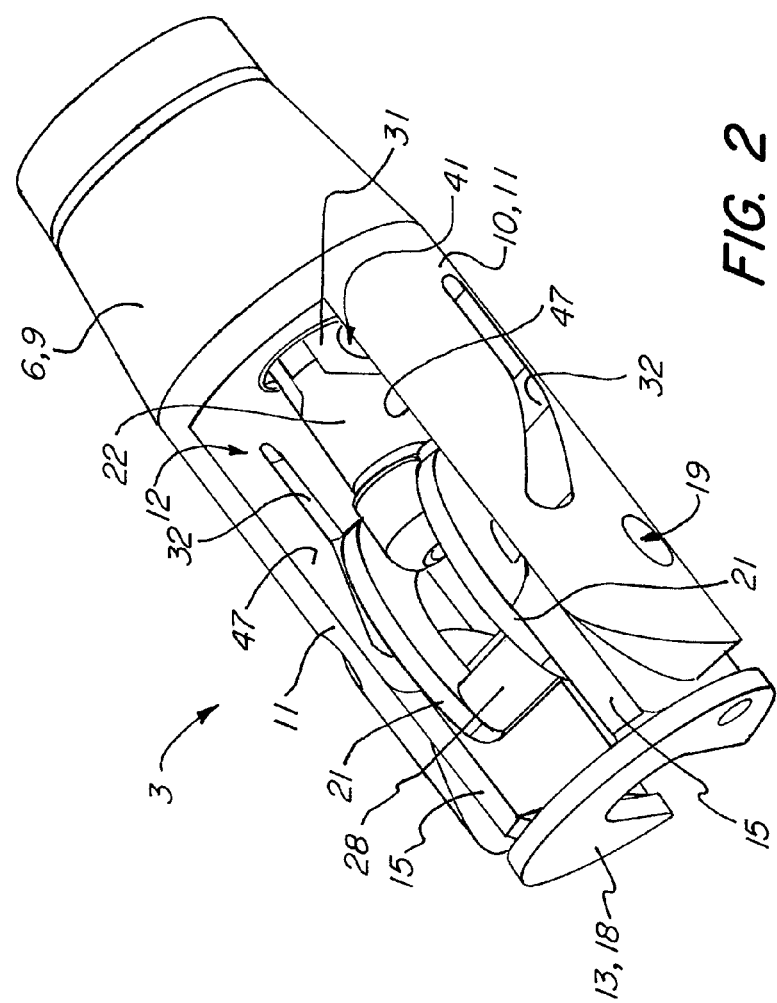
FIG. 2 shows the distal instrument part of the instrument from FIG. 1 in a perspective view from diagonally above.

With reference to FIGS. 1 through 6, an instrument is now described that is designated as a whole as reference number 1. Related positional and directional indications here such as "above" or "below," for the purpose of simpler description, refer merely to the positioning of the instrument 1 in the drawings. It goes without saying that the instrument 1 can be aligned in other ways, so that these indications are in no way to be understood as restrictive.

The instrument 1 described in connection with the drawings serves in particular to modify and/or to fix an organ in its position, for example for conducting laparascopic investigations or treatments.

The instrument 1 includes a proximal instrument part 2 and a distal instrument part 3 that are connected with one another by a tubular shaft 4 that is shown shortened in FIG. 1. A longitudinal direction or longitudinal axis 33 of the instrument 1 is defined by the tubular axis of the shaft 4.

The proximal instrument part 2 is connected with the proximal end of the shaft 4 with an attachment 7 connected firmly with the handle 8 for holding the instrument 1. The attachment 7 is connected on the handle 8 by a conventional connection, which for example is removable, such as a screw-in or catch-lock connection. For this purpose the attachment 7 can for example be provided with a tubular support (not shown) onto which the handle 8 is pushed. In corresponding manner the shaft 4 is applied in conventional manner on the attachment 7, for example removably. The handle 8 includes a first gripping part 49 rigidly connected with the attachment 7 as well as a second gripping part 50 that can be pivoted on the pivot hinge 51 with respect to the first gripping part 49.

The distal instrument part 3 comprises a swivel head 6 that is mounted on the distal end of the shaft 4 by a connector part 5, such that the swivel head 6 is affixed on the connector part 5 by a conventional removable connection, such as a screw-in or catch-lock connection. The connector part 5 is applied removably or else nonremovably on the shaft 4 in conventional manner.

The swivel head 6 is provided with a base portion 9 that widens radially toward the distal end of the instrument 1 and on which a hinged portion 10 with two hinged forks 11 parallel to one another connects distally. The two hinged forks 11 extend along the longitudinal axis 33 and form between themselves an approximately rectangular recess 12 with two level inner surfaces 47 facing one another. They serve to connect a pivot part 13 on the swivel head 6.

The pivot part 13 is provided with two pivot arms 15, which are surrounded by the two hinged forks 11. To provide hinged connection with the hinged forks 11, the two pivot arms 15 comprise through-holes, which are not shown in detail and which are penetrated by a first hinged pin 17, which engages in first bearing holes 16 of the hinged forks 11, said holes 16 being opposite one another. In a first variant, the first hinged pin 17 is mounted so that it can rotate in the first bearing holes 16, while the pivot arms 15 are connected nonrotatably with the first hinged pin 17. In a second variant, the first hinged pin 17 is mounted nonrotatably in the first bearing holes 16, while the pivot arms 16 are rotatably connected with the first hinged pin 17. Alternatively it would be equally possible that instead of the first hinged pin 17 a hinged stud is foreseen between the pivot arm 15 and the neighboring hinged fork 11, and through said stud the pivot arm 15 can be pivoted with respect to the hinged fork 11.

Accordingly the pivot part 13 is pivotably mounted on the swivel head 6 by a pivot hinge, designated altogether with the reference number 19 and hereinafter referred to as "pivot part hinge." By the location and orientation of the first hinge pin 17 a first pivot axis 29 is defined, which is perpendicular to the longitudinal axis 33.

The two pivot arms 15 of the pivot part 13 are connected with one another by a carrier plate 18 positioned perpendicularly to the longitudinal axis 33. The carrier plate 18, located outside the recess 12 formed by the two hinged forks 11, serves to detachably mount a device (not illustrated) that is required for manipulation of the organ corresponding to the specific demands and whose spatial position can be modified by pivoting the pivot part 13. It would also be possible to connect such a device without carrier plate 18 directly with the two pivot arms 15.

The pivot part 13 is coupled with a translationally movable push/pull rod 20 (designated in the description introduction as "actuation element"). The push/pull rod 20 is incorporated in a hollow space of the tubular shaft 4 and extends proximally through the attachment 7 as far as the handle 8 and distally into the swivel head 6. It can be moved back and forth by means of a manually actuatable mechanism to generate a translational movement, so that it acts as a traction or pressure rod depending on the respective movement direction. In the embodiment illustrated in FIG. 1 the push-pull rod 20 for this purpose is firmly connected with a fastening portion 52 of the second gripping part 50 (not shown), so that it can be pushed translationally by actuating the handle 8. To reduce friction it is enclosed within a sheath 30 made of a low-friction material. Mechanisms of this type to move the push-pull rod 20 are familiar to the specialist both from relevant patent literature and from commercially available instruments.

The pivot part 13 can be pivoted into positions at various angles to the shaft 4 or longitudinal axis 33 by the push-pull rod 20, which can move bidirectionally along the longitudinal axis 33. For this purpose an effective coupling is foreseen that includes arch-shaped coupling parts 21 extending in the longitudinal axis 33 that are in a hinged connection both with the push-pull rod 20 and with the two pivot arms 15 of the pivot part 13. In particular, the proximal ends of the coupling parts 21 are connected on a distal end portion of the push-pull rod 20, namely a rod head 22 that is in hinged connection with the other rod portion 31. For a hinged connection between the rod head 22 and the two coupling parts 21 enclosing the rod head 22 in fork-like manner, the rod head 22 is equipped with a first through-hole 23 that is connected flush with the second through-holes 24 of the two coupling parts 21. The first and second through-holes 23, 24 are penetrated by a second hinged pin 25 that is mounted with both its ends on the hinged forks 11. To mount the second hinged pin 25, the two hinged forks 11 are provided with connecting links 32 configured as openings in which the ends of the second hinged pin 25 are inserted. In a first variant, either the two coupling parts 21 or the rod head 22 is nonrotatably connected with the second hinged pin 25, while the second hinged pin 25 is mounted rotatably and slidably in the connecting links 32. In a second variant the coupling part 21 and the rod head 22 are connected rotatably with the second hinged pin 25, while the second hinged pin 25 is mounted nonrotatably but slidably in the connecting links 32.

Accordingly, the two coupling parts 21 are mounted pivotably on the rod head 22 by means of a hinge, designated as a whole with the reference number 36 and hereinafter designated as "proximal coupling part hinge." By the location and orientation of the second hinged pin 25, a second pivot axis 37 is defined that runs perpendicular to the longitudinal axis 33 or parallel to the first pivot axis 29 of the pivot part 13.

The two coupling parts 21 are each in hinged connection with a pivot arm 15 on their other ends, so that the two pivot arms 15 enclose the coupling parts 21 in fork-like manner. Alternatively, a configuration is also possible in which the coupling parts 21 enclose the two pivot arms 15 or else one coupling part 21 is applied with reference to the longitudinal axis 33 on the outside, and the other on the inside of its associated or selected pivot arm 15. For a hinged connection of the coupling parts 21 with the pivot arms 15, the coupling parts 21 are each provided with second bearing bore-holes 26 in which a hinged stud 27 is rotatably inserted that is shaped on the adjoining pivot arm 15. Alternatively it would be equally possible for the hinged studs 27 to be shaped on the coupling parts 21 and rotatably inserted in corresponding bearing bore-holes of the pivot arms 15.

Accordingly, the two coupling parts 21 are pivotably mounted on the pivot arms 15 by means of a hinge that is designated as a whole with reference number 39 and referred to hereinafter as "distal coupling hinge." By the location and orientation of the two hinged studs 27, a third pivot axis 40 is defined that runs perpendicular to the longitudinal axis 33 or parallel to the second pivot axis 37.

The two coupling parts 21 engage outside the first pivot axis 29 on the two pivot arms 15, so that between the point of engagement of the distal coupling part hinge 39 and the first pivot axis 29 a lever is formed by which a torque can be transmitted to pivot the pivot part 13. Between the two coupling parts 21 a distancing part 28 is provided in the area of the distal coupling part hinge 39, and by means of said distancing part 28 the two coupling parts 21 are stiffened with respect to one another.

In a translational movement of the push-pull rod 20, the connecting links 32 serve as a connecting link guide for the second hinged pin 25 of the proximal coupling hinge 36, so that the two ends of the second hinged pin 25 engage as connecting studs 48 in the connecting links 32. In the present embodiment, the connecting links 32 are configured as perforations of the hinged forks 11. Alternatively, it would be equally possible to configure the connecting links 32 for example as groove-type indentations of the inner surfaces 47 of the hinged forks 11 that face one another.

The two connecting links 32 have an angular shape in a plane that extends from the longitudinal axis 33 and from a perpendicular line to each of the pivot axes 29, 37, 40. Going from proximal to distal, they are made up of a (linear) longitudinal portion 34 that extends along the longitudinal axis 33 and a (linear) diagonal portion 35 extending diagonally to the longitudinal axis 33 and are of approximately equal length. In the drawings the diagonal portion 35 of the connecting links 32 is positioned with respect to the longitudinal axis 33 in such a way that torque is exerted on the pivot part 13 by the distal coupling part hinge 39 upon pushing the push-pull rod 20. On the basis of a plane that is spanned by the longitudinal axis 33 and the first pivot axis 29 of the pivot part hinge 19, the diagonal portion 35 extends for this purpose from the proximal to the distal in that semi-space in which the distal coupling part hinge 39 is located. In the embodiment shown in the drawings, the diagonal portion 35 is at an angle upward to the longitudinal axis 33, so that an angle between the diagonal portion 35 and the longitudinal axis 33, for example, is approximately 30 degrees. However, a different angle can be foreseen, depending on the type and arrangement of the hinged coupling between the pivot part 13 and the push-pull rod 20.

In order that the rod head 22 can follow the nonstraight movement track imposed by the two connecting links 32, the rod head 22 is hinged on the remainder of the rod portion 31 by a hinge, which is designated as a whole with reference number 41 and referred to hereinafter as "rod head hinge." For this purpose the distal end of the rod portion 31 is provided with third bore-holes 42, which are penetrated by a third hinge pin 43. A fourth pivot axis 44 is defined by the third hinge pin 43 and aligned perpendicular to the longitudinal axis 33 so that the swivel head 6 can follow the course of the diagonal portion 35.

The proximal coupling hinge 36, in the translational pushing motion of the push-pull rod 20, is directly controlled by the connecting links 32 in order to pivot the pivot part 13, so that a distal end stop 45 formed by the diagonal portion 35 and a proximal end stop 46 formed by the longitudinal portion 34 each provide end points for the bidirectional translational movement of the push-pull rod 20 or its distal rod head 22.

Figure 3:
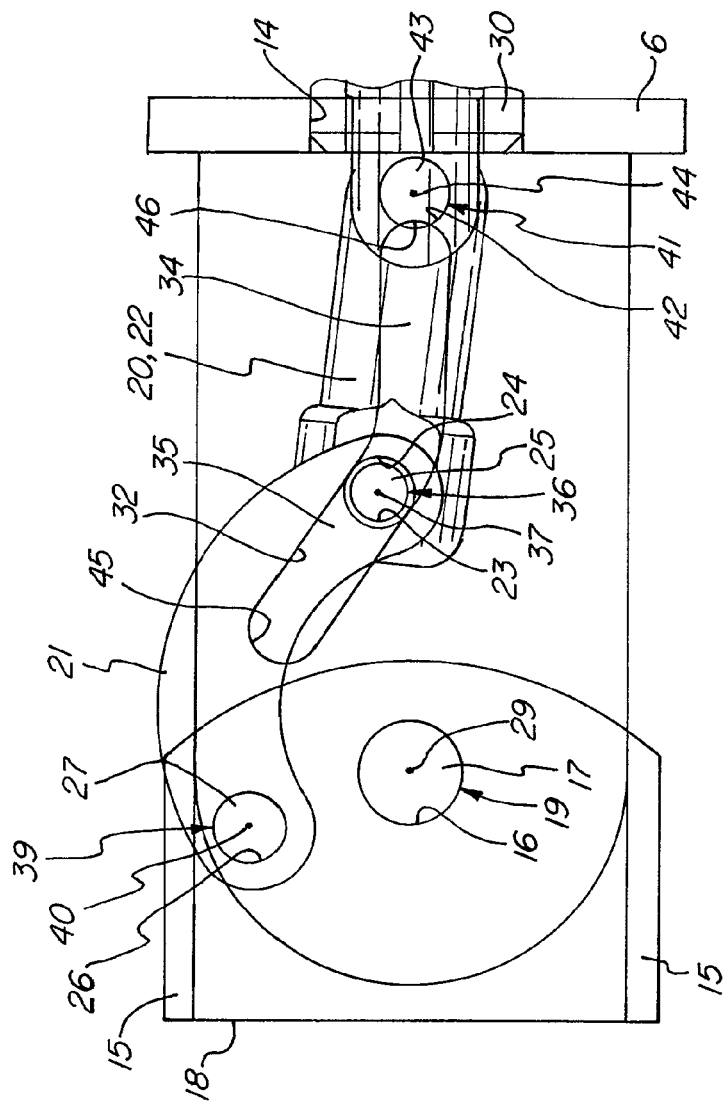
FIG. 3 shows the distal instrument part of the instrument from FIG. 1 in a transparent side view.
Figure 4:
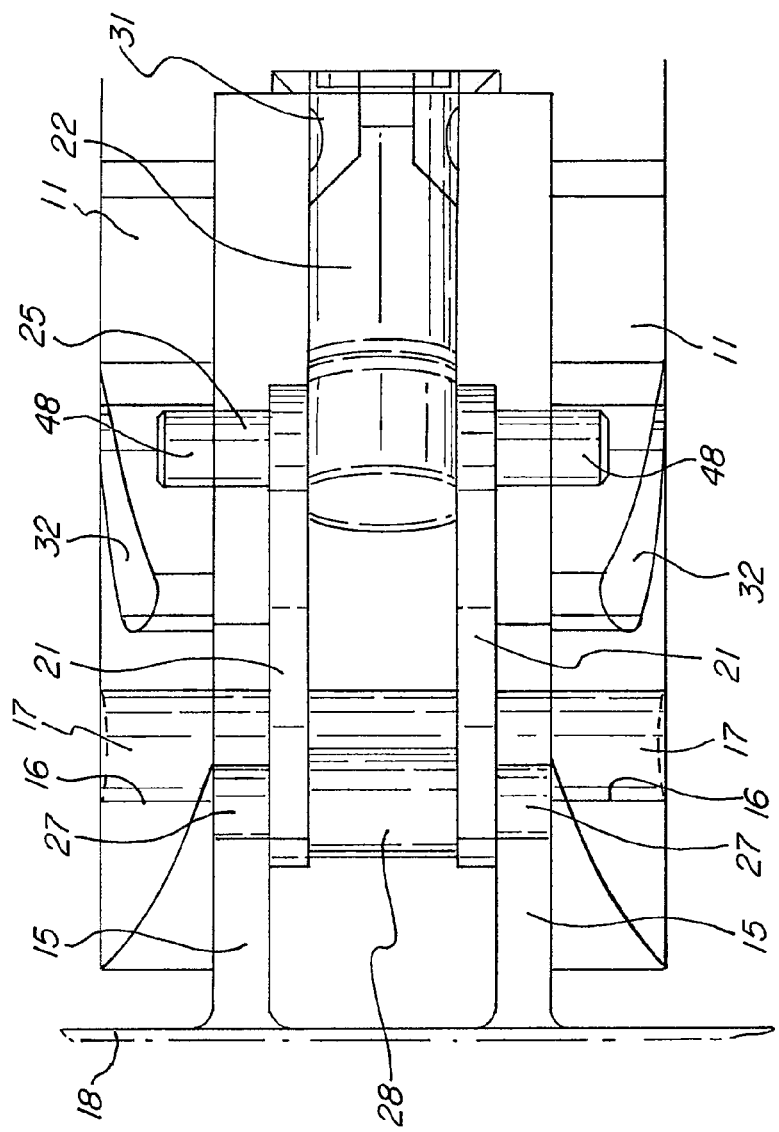
FIG. 4 shows the distal instrument part of the instrument of FIG. 1 in a partially transparent view.

FIG. 3 shows a situation in which the proximal coupling part hinge 36 is located approximately in the middle position with respect to the bidirectional stroke of the push-pull rod 20. An angle position of the pivot part 13 parallel to the longitudinal axis 33 is here associated, for example, with the middle position of the push-pull rod 20. The pivot part 13 thus has no displacement with respect to the shaft 4 (angle position zero degrees). Alternatively it is also possible that the pivot part 13, with the push-pull rod 20 at middle position in relation to the shaft 4, has an angle position different from zero degrees.

Figure 5:
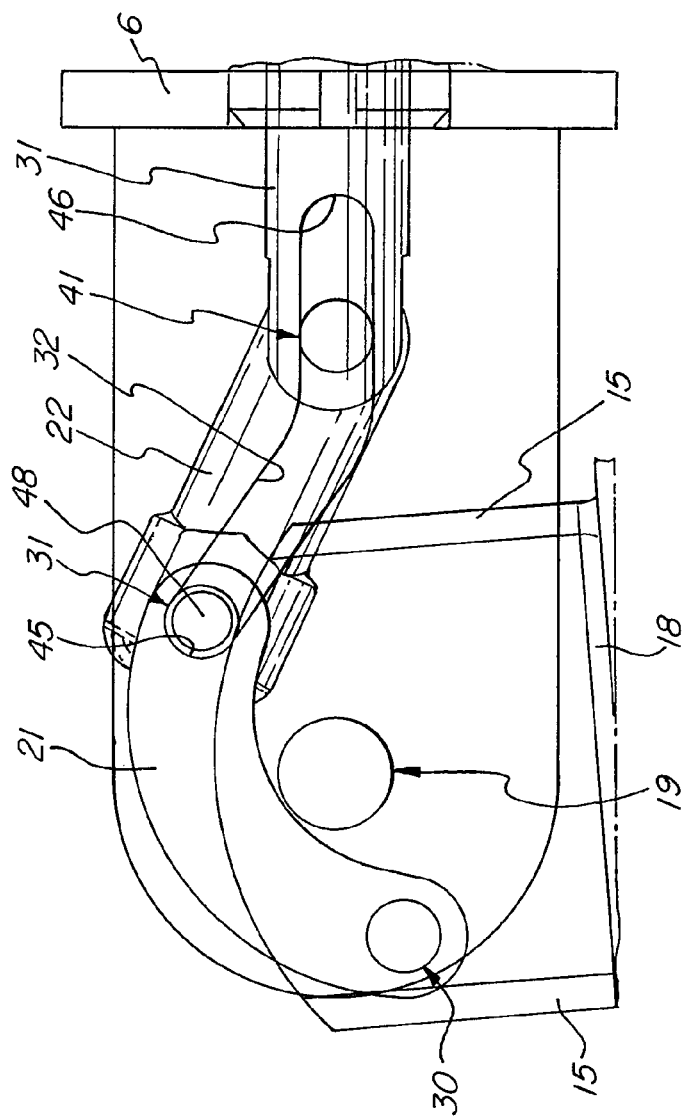
FIG. 5 shows the distal instrument part of the instrument of FIG. 1 in a partially transparent side view with one pivot part pivoted in one rotary direction.

If the push-pull rod 20 is pushed in the distal direction out of its middle position, the consequence is that the pivot part 13 is pivoted by the two coupling parts 21 in the one rotation direction (counterclockwise in the drawings) until the connecting link studs 48 of the second hinge pin 25 of the proximal coupling hinge 36 become contiguous with the distal end stop 45 of the connecting links 32. FIG. 5 depicts a situation in which the connecting link studs 48 are contiguous with the distal end stop 45, corresponding to a maximum stroke of the push-pull rod 20 in the distal direction. With respect to the shaft 4, the pivot part 13 assumes an angle position of about +120 degrees (here designated for example with positive degree figures).

Figure 6:
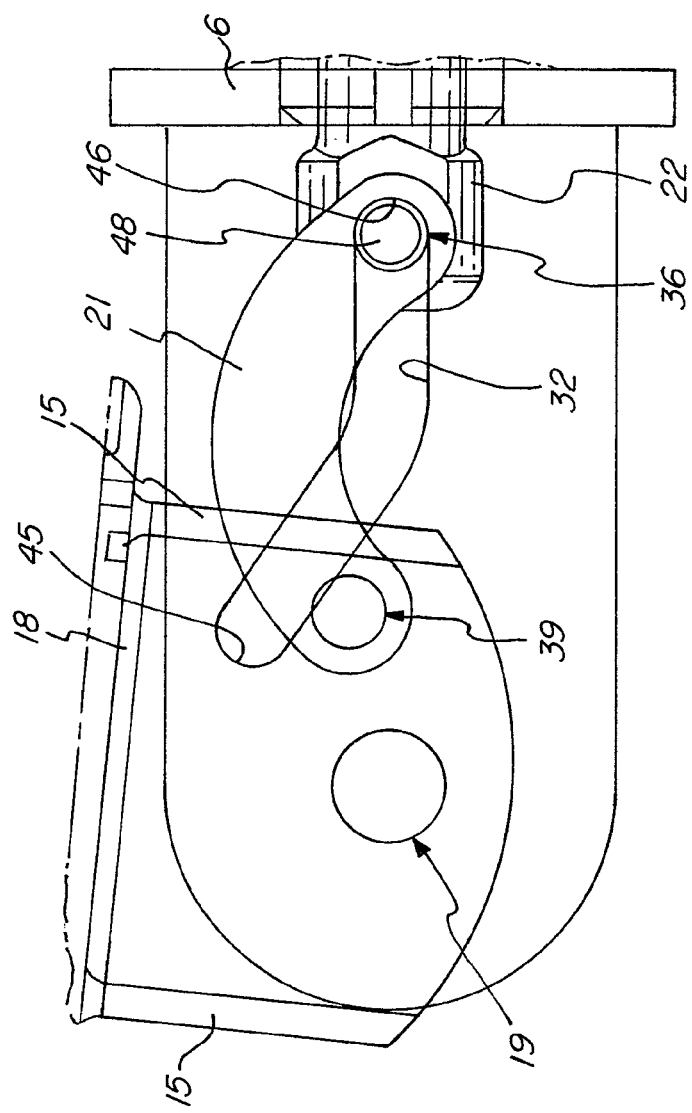
FIG. 6 shows the distal end portion of the instrument of FIG. 1 in a partially transparent side view with one pivot part pivoted in the other rotary direction.

If the push-pull rod 20 is pushed translationally in the proximal direction out of its middle position in the opposite movement direction, the pivot part 13 is pivoted by the two coupling parts 21 in the opposite rotary direction, that is, counterclockwise in the drawings, until the connecting link studs 48 of the second hinge pin 25 become contiguous with the proximal end stop 46 of the connecting links 32. Shown in FIG. 6 is a situation in which the connecting link studs 48 are contiguous with the proximal end stop 46, corresponding to a maximum stroke of the push-pull rod 20 in the proximal direction. With respect to the shaft 4, the pivot part 13 in this position has a displacement of about minus 120 degrees (here, for example, designated with positive degree figures).

Accordingly the pivot part 13, starting from a middle position in which the two pivot arms 15 extend parallel to the shaft 4, can be pivoted by back-and-forth motion of the push-pull rod 20 both in the one rotation direction and in the other.

Owing to the arched configuration of the coupling parts 21, the pivot part 13 can be pivoted advantageously over a relatively broad pivot range without their colliding with the first hinge pin 17 of the pivot part hinge 19 that connects the two hinged forks 11 with one another. However, instead of arched coupling parts 21, it is equally possible to provide coupling parts of different shape. For example, straight coupling parts could be used, but in this case possibly the first hinge pin 17 of the pivot part hinge 19 should be replaced by respective hinge studs between the hinged forks 11 and the pivot arms 15.

Likewise, instead of the rod head 22 hinged onto the rod portion 31 by means of the rod head hinge 41, a flexible push-pull rod 20 can be provided whose distal end portion is capable of following the movement track imposed by the connecting links 32.

Conventional generic instruments are advantageously improved by the inventive instrument 1, so that the pivot part 13 becomes pivotable in both pivot directions via a coupling that is simple to achieve by means of a translationally movable push-pull rod 20.

What is claimed is:

1. A medical instrument with a proximal instrument part and a distal instrument part that are connected with one another by an elongated shaft, such that the distal instrument part includes a pivot element that is mounted to pivot with respect to the shaft and that is pivotable by means of a translationally movable actuation element, wherein
    the pivot element is coupled with the actuation element by means of at least one coupling element, so that the coupling element is in a hinged connection with the pivot element by a first hinged connection and with the actuation element by a second hinged connection,
    the second hinged connection of the coupling element is controlled by at least one nonlinear channel or nonlinear groove formed by the distal instrument part in such a way that the pivot element is pivotable both in one pivot direction as well as in the other pivot direction, and
    the nonlinear channel or nonlinear groove is configured to guide the actuation element in nonlinear movement.

2. The medical instrument according to claim 1, wherein the nonlinear channel or nonlinear groove is of angular configuration, with a longitudinal portion extending in the longitudinal axis of the shaft and a diagonal portion extending diagonally to the longitudinal axis.

3. The medical instrument according to claim 1, wherein the second hinged connection of the coupling element is directly controlled by the nonlinear channel or nonlinear groove.

4. The medical instrument according to claim 3, wherein the nonlinear channel or nonlinear groove is configured as a connecting link guide.

5. The medical instrument according to claim 4, wherein the second hinged connection of the coupling element includes at least one hinged member that grips in the connecting link guide.

6. The medical instrument according to claim 2, wherein the second hinged connection of the coupling element is controlled directly by the nonlinear channel or nonlinear groove.

7. The medical instrument according to claim 1, wherein the actuation element comprises a distal end portion that is pivotably hinged onto a different portion of the actuation element.

8. The medical instrument according to claim 1, wherein the actuation element is flexible.

9. The medical instrument according to claim 1, characterized by at least one arch-shaped coupling element.

10. The medical instrument according to claim 1, wherein the distal instrument part includes a forked portion to hinge the pivot element.

11. The medical instrument according to claim 1, wherein the pivot element, starting from a middle position, is pivotable by at least 90 degrees in the one pivot direction and at least 90 degrees in the other pivot direction.

* * * * *